(12) United States Patent
Roncarolo et al.

(10) Patent No.: US 8,329,637 B2
(45) Date of Patent: Dec. 11, 2012

(54) METHOD FOR THE TREATMENT OF AUTOMIMMUNE DISEASES COMPRISING ADMINISTERING RAPAMYCIN AND IL-10

(75) Inventors: Maria Grazia Roncarolo, Segrate (IT); Manuela Battaglia, Milan (IT)

(73) Assignee: Maria Grazia Roncarolo, Segrate (IT)

( * ) Notice: Subject to any disclaimer, the term of this patent is extended or adjusted under 35 U.S.C. 154(b) by 313 days.

(21) Appl. No.: 11/839,676

(22) Filed: Aug. 16, 2007

(65) Prior Publication Data

US 2008/0069797 A1 Mar. 20, 2008

Related U.S. Application Data

(62) Division of application No. 10/536,316, filed as application No. PCT/EP03/13351 on Nov. 27, 2003, now abandoned.

(60) Provisional application No. 60/429,561, filed on Nov. 29, 2002.

(51) Int. Cl.
*A61P 37/06* (2006.01)
*A61P 19/02* (2006.01)
*A61K 38/20* (2006.01)
*A61K 31/436* (2006.01)
*C07K 17/08* (2006.01)
*C07K 14/54* (2006.01)

(52) U.S. Cl. ........ 514/1.1; 514/7.3; 514/16.6; 514/17.9; 514/825; 514/866; 530/399; 530/402; 930/141

(58) Field of Classification Search .......................... None
See application file for complete search history.

(56) References Cited

U.S. PATENT DOCUMENTS

| 5,368,854 | A | 11/1994 | Rennick |
| 6,428,985 | B1 | 8/2002 | Bromberg et al. |
| 2002/0044921 | A1* | 4/2002 | Lee et al. ..................... 424/85.2 |

FOREIGN PATENT DOCUMENTS

| EP | 770393 | 5/1997 |
| WO | WO 94/17773 | 8/1994 |

OTHER PUBLICATIONS

Shapiro et al (2000. The New England Journal of Medicine. 343(4): 230-238).*
Wells (1990) Biochemistry 29(37): 8509-8517.*
Ngo et al (1994) "The Protein Folding Problem and Tertiary Structure Prediction, Chapter 14: Computational Complexity Protein Structure Prediction, and the Levinthal Paradox" pp. 433-440 and 492-495 only.*
Bork (2000) Genome Research 10:398.*
Skolnick et al (2000) Trends in Biotech. 18(1): 34.*
Doerks et al (1998) Trends in Genetics 14(6): 248.*
Brenner (1999) Trends in Genetics 15(4): 132.*
Battaglia et al #1 (2006. Diabetes. 55: 40-49).*
Battaglia et al #2 (2006. Diabetes. 55: 1571-1580).*
Experimental Transplantation:Stem Cells Mobilization, XP009027131, Battaglia et al, 2002. Blood. 100(11):610a. Abstract No. 2405.

* cited by examiner

*Primary Examiner* — Zachary Howard
(74) *Attorney, Agent, or Firm* — Young & Thompson

(57) ABSTRACT

The invention discloses a combined preparation containing IL-10 and rapamycin, able to induce immunosuppression and antigen-specific immune tolerance, and the use thereof in the treatment of diseases involving an excessive, dysfunctional or uncontrolled immune responses mediated by T cells.

14 Claims, 12 Drawing Sheets a)

± treatment

NOD pre-diabetic
11 weeks old b)

| # of mice | treatment | diabetic mice 17 weeks |
|---|---|---|
| 6 | none | (2/6) 33% |
| 7 | rapamycin | (1/7) 14% |
| 3 | rapamycin+IL-10 | (0/3) 0% |
| 7 | IL-10 | (1/7) 14% | a)

b)

| # of mice | cells transferred in NOD SCID mice | treatment | Diabetic mice |
|---|---|---|---|
| 3 | 5X10$^6$ diabetogenic | none | (3/3) 100% |
| 4 | 5X10$^6$ diabetogenic | rapa, antiTac, FK506 | (4/4) 100% |
| 3 | 5X10$^6$ diabetogenic | rapa, antiTac, IL-10 | (1/3) 33% |
| 4 | 5X10$^6$ diabetogenic | rapa, antiTac | (3/4) 75% |

METHOD FOR THE TREATMENT OF AUTOIMMUNE DISEASES COMPRISING ADMINISTERING RAPAMYCIN AND IL-10

The present invention regards methods and compositions for inducing immunosuppression and/or antigen-specific immune tolerance in subjects in need thereof. More precisely, the invention provides a combined preparation of rapamycin and IL-10 for use in the treatment of diseases involving an excessive, dysfunctional or uncontrolled self- or non-self immune response mediated by T cells. The invention is also directed to pharmaceutical compositions containing IL-10 and rapamycin and to their use as modulators of the immune response.

BACKGROUND OF THE INVENTION

Transplantation and immunosuppressive drugs. Transplantation is the treatment of choice for most patients with end stage kidney-failure, hearth or liver disease, autoimmune type 1 diabetes and it is a developing possibility for patients with deficiencies in small-bowel and lung function. Graft survival depends on a number of factors but the most significant of these is the administration of powerful immunosuppressive drugs. Transplantation between genetically disparate individuals evokes a rapid and potentially destructive alloreactive immune response that, if left uncontrolled, can lead to complete destruction of the transplanted organ. Administration of immunosuppressive drugs attenuates this response and thus prevents acute graft rejection. However, continued graft survival depends on life-long immunosuppression because withdrawal of immunosuppression results in re-activation of the rejection response, leading to rapid graft destruction.

Recently, among the immunosuppressive drugs, selective T cell inhibitors have been developed including cyclosporine A (CsA), FK506 and rapamycin. Both CsA and FK506 inhibit T cell activation by blocking calcineurin function and thereby prevent the generation of the potent nuclear factor of activated T cells (NFAT). This step is essential for up-regulating the mRNA of several cytokines, including IL-2. The major limitations of CsA and FK506 are their various toxicities. Moreover, both CsA and FK506 prevent T cell apoptosis (reviewed in Yu et al. 2001).

On the contrary, rapamycin is a potent immunosuppressant that inhibits T cell proliferation by binding a cytosolic protein (FKBP-12) and blocking IL-2 signaling (Sehgal 1998). The complex binds to and blocks the mammalian target of rapamycin (mTOR), resulting in the inhibition of cytokines induced T-cell proliferation. Importantly, in contrast to CsA and FK506, rapamycin does not block TCR-mediated T cell activation (Blaha et al, 2003) and IL-2 T cell priming for activation-induced cell death (AICD). This latter is a form of T cell apoptosis which seems to play a role in the induction of peripheral transplantation tolerance (Wells et al. 1999). Unlike CsA, which has no effects on dendritic cells (DC), rapamycin profoundly affects DC phenotype and function (Hackstein et al. 2002). It markedly reduces their antigen uptake capacity, thereby favoring the differentiation of DC with a tolerogenic phenotype. This effect, present at a low, physiologically relevant concentration of rapamycin (1 ng/ml) is independent of DC maturation and has been demonstrated both in vitro and in vivo (Hackstein et al. 2002).

Although the currently available immunosuppressive drugs are very effective in short term, substantial problems indicate a pressing need to develop alternative and more sophisticated ways of preventing graft rejection. The main obstacle is the inability to distinguish between beneficial immune responses against infectious pathogens and destructive immune responses against the graft. Thus, immunosuppressive therapies can lead to increased risk of opportunistic infections. Several studies show that non specific immunosuppression would lead to an increased incidence of cancer in transplanted patients (Hojo et al. 1999). Therefore, the full potential of transplantation will be fulfilled only when alternatives to non specific immunosuppression are found. The major aim of transplantation immunology is to develop protocols that prevent immune responses towards the graft but leave the rest of the immune system intact. This accomplishment will lead to transplantation tolerance.

Autoimmunity. In autoimmune diseases, undesired immune responses to self-antigens lead to destruction of peripheral tissues. Treatments of autoimmune diseases are currently based on downmodulation of inflammation and non-antigen (Ag) specific immunosuppression. As for prevention of allograft rejection, this strategy is frequently not effective in the long term with high risk of relapse once the drug is withdrawn and hazards of excessive immunosuppression, including infections and tumors. The alternative approach is based on the induction of transient immunosuppression and/or specific immune tolerance, aimed at "silencing" the pathogenic response to self-Ag, while keeping host defense mechanism intact.

The immune system has evolved two distinct mechanisms to induce tolerance to self or non-harmful antigens. These are referred to as central and peripheral T cell tolerance. Central tolerance is realised during fetal development and the very early natal period and is mediated by clonal deletion of self-reactive T cells during thymic development. Peripheral mechanisms induce tolerance in mature T cells and occur in the periphery during the whole life. These mechanisms include functional inactivation of antigen specific lymphocytes (named anergy) and activation of T cell subsets with suppressive and regulatory capacities (T regulatory cells reviewed in Battaglia et al. 2002), Tolerance and T regulatory cells. Recently, there has been a growing interest in the induction of T regulatory (Tr) cells as a strategy to achieve graft specific tolerance. The majority of Tr cells identified to date lie within the $CD4^+$ population, although other T cell subsets, such as $CD8^+$, $CD8^+CD28^-$ and $TCR^+CD4^-CD8^-$ have also been shown to contain cells with regulatory capacity. Within the $CD4^+$ population, various fractions with suppressive properties have been identified. Our group has characterised a subset of Tr cells, defined as type 1 regulatory T cells (Tr1), which have a cytokine production profile distinct from that of Th1 and Th2 cells. Human and mouse Tr1 cells produce high levels of IL-10, significant amounts of IL-5, TGF-β, and IFN-γ, but low levels of IL-2 and no IL-4 (Groux et al. 1997). IL-10 is a crucial cytokine for the differentiation and effector functions of Tr1 cells. Culture of $CD4^+$ T cells in the presence of antigen and IL-10 leads to generation of Tr1 cells that are able to suppress antigen-specific T cell responses in vitro and the development of autoimmune colitis in vivo (Groux et al. 1997). Tr1 cells can also be generated in vivo. Tr1 cells have indeed been isolated from peripheral blood of SCID-reconstituted patients, in whom high levels of IL-10 were associated with successful allogeneic stem cell transplantation (Bacchetta et al. 1994).

Tolerance and IL-10. IL-10 plays a key role in immunoregulation (reviewed in Moore et al. 2001). It inhibits proliferation and IL-2 production of T lymphocytes. IL-10 has strong anti-inflammatory properties by inhibiting production of pro-inflammatory cytokines such as TNF-α, IL-1, IL-6 and chemokines such as IL-8, MIP1α, and MIP1β by activated monocytes/macrophages, neutrophilis, eosinophilis, and mast cells. Moreover, IL-10 suppresses antigen-presenting capacities of antigen presenting cells such as monocytes/macrophages/DC by downregulating MHCII and co-stimulatory molecules. The ability of IL-10 to inhibit induction and effector function of T cell-mediated and anti-inflammatory immune responses led to numerous studies on IL-10 expression, function, and potential utility in bone marrow and organ transplantation. In studies of vascularized heart allograft in mice, IL-10 treatment of recipient animals prior to grafting enhanced graft survival, whereas providing IL-10 at or after the time of grafting had little beneficial effect or even enhanced rejection (Li et al. 1999). Patients exhibiting elevated levels of IL-10 production prior to BMT have lower incidence of GVHD and improved survival (Baker et al. 1999). On the contrary, high IL-10 levels in post-BMT GVHD patients indicates a poor prognosis for survival (Hempel 1997). However, Blazar and colleagues showed that treatment of mice with small amounts of IL-10 ($10^{-3}$, $10^{-4}$ of the amount that increased mortality) protects against GVHD-associated lethality (Blazar et al. 1998).

Combination of immunosuppressive drugs with IL-10. The majority of immunosuppressive drugs in current clinical uses act by inhibiting T cell activation and thus prevents graft rejection. However, this may be counter-productive, as under appropriate circumstances, T cell activation may lead to the induction of processes facilitating the development of graft-specific tolerance. Therefore, the usage of immunosuppressive drugs might not be optimal when the aim is tolerance induction. A clear demonstration of this phenomenon comes from SCID patients in whom tolerance was achieved after allogeneic hematopoietic stem cell transplantation without any immunosuppressive therapy (Bacchetta et al. 1994). In these patients the presence of donor derived Tr1 cells specific for the host alloantigens correlated with stable mixed chimerism, high levels of IL-10 production in vivo, and normal immune functions in the absence of any immunosuppressive therapy. In contrast, in BMT patients who received an immunosuppressive regimen to control acute-GVHD, Tr1 cells could not be isolated from peripheral blood, although donor derived T cells specific for host alloantigens were detectable (Bacchetta et al. 1995).

Rapamycin represents a novel compound with interesting immuomodulatory properties. For this reason we combined the in vivo administration of rapamycin with IL-10 in order to prevent allograft rejection or modulate type 1 diabetes and to allow the in vivo development of Tr cells.

STATE OF THE ART

U.S. Pat. No. 6,277,635 relates to the use of IL-10 for suppressing transplant rejection. This patent teaches methods of treating and inhibiting tissue rejection, inhibiting GVHD and antigen specific responses. It further describes T cells that exhibit anergy for a particular antigen.

U.S. Pat. No. 6,428,985 describes mammalian, including human, immunosuppressive compositions containing IL-10 polypeptides with at least one mutation in the native sequence (Mut IL-10), either alone or in combination with other agents, and various in vitro and in vivo methods of using such compositions and combinations thereof. Uses include immunosuppressive and combination therapies for a number of diseases and disorders related to inflammation, transplantation, fibrosis, scarring, and tumor treatment. The effect of Mut IL-10 has been shown in animal studies but not in human clinical settings.

U.S. Pat. No. 5,624,823 describes DNA encoding porcine IL-10 and a method for inducing tolerance in a recipient mammal, e.g. a primate, receiving an allogeneic transplant. Rapamycin, cyclosporine and FK506 are mentioned as "help reducing agent", i.e. agents which reduce the cytokine release. Porcine IL-10 is used in a context of thymus transplantation only.

U.S. Pat. No. 6,022,536 describes the combined use of IL-10 and cyclosporine as immunosuppression therapy for treating autoimmune diseases and GVHD. Synergistic combination of low doses of IL-10 and cyclosporine and a pharmaceutical carrier are proposed.

U.S. Pat. No. 6,403,562 describes methods for treating autoimmune-related diseases, such as multiple sclerosis, by administering IL-10 together with TGF-β, to a person afflicted with or predisposed to an autoimmune disease. These cytokines act in a synergistic manner as suppressor factors to inhibit the activation of self-reactive T cells that are involved in autoimmune disease.

DESCRIPTION OF THE INVENTION

The invention provides a combined pharmaceutical preparation containing IL-10 and rapamycin for use in the modulation of T-cell mediated immune response, in particular for inducing immunosuppression and antigen-specific immune tolerance in a subject in need thereof. The induction of Tr1 and $CD4^+CD25^+$ Tr cell-mediated antigen-specific immune tolerance is useful for the treatment of pathological conditions that involve an excessive, dysfunctional, unregulated or uncontrolled self- or non-self T cell-mediated immune response.

In a preferred embodiment of the invention, IL-10 and rapamycin are in the form of a combined preparation for simultaneous, separate or sequential use in the preventive or therapeutic treatment of allogeneic organ rejection, type 1 diabetes, autoimmune and chronic inflammatory diseases including psoriasis, multiple sclerosis, inflammatory bowel disease, Crohn's disease, rheumatoid arthritis, or other T-cell mediated diseases such as GVHD, asthma, atopic dermatitis, chronic obstructive pulmonary disease, and immune reactions to gene therapy derived products. In addition, treatment of fibrotic diseases including liver and lung fibrosis is envisaged.

Preferably, the combined preparation is used for the preventive or therapeutic treatment of solid allogeneic organ rejection, particularly allograft β-islets rejection, and autoimmune diseases, especially type 1 diabetes.

The combined preparation may contain human or viral IL-10, analogs, derivatives or conjugates thereof improving the bioavailability or biological efficacy of the natural molecule, such as polyethylene glycol (PEG) conjugated IL-10. IL-10 functional analogs include small molecules that mimic IL-10 effects and monoclonal antibodies (mAbs) against the IL-10 receptor or IL-10 fusion proteins, which trigger IL-10 signaling pathway.

The combined preparation may contain rapamycin analogs or derivatives. Besides rapamycin and IL-10, derivatives or analogs thereof, the combined preparation may further contain immunosuppressants or immunomodulating agents, monoclonal antibodies or cytokines. Preferred biologically active substances that may be used in combination with IL-10 and rapamycin include: a) calcineurin inhibitors such as cyclosporine, FK506 (tacrolimus), pimecrolimus, b) other immunosuppressant such as micofenolate, c) antibodies against different isoforms of CD45, or adhesion molecules such as LFA-1 and d) antibodies against the IL-2 receptor alpha, beta and gamma chains. Suitable immunosuppressive agents include those that act through the IL-2 signaling pathway (e.g. JAK1 and JAK3 and STAT5 inhibitors). The combination of rapamycin+antiTac (a humanized antibody to the IL-2 receptor α chain)+IL-10 proved particularly effective in preventing allogeneic rejection, especially in a murine model of allograft β-islets rejection, by inducing a state of tolerance instead of the persistent immunosuppression generated by conventional therapeutic protocols. Moreover, the combination of rapamycin+IL-10 proved to be effective in treating autoimmune diabetes and inducing long term immunomodulation in NOD mice. Tolerance is achieved as a result of the rapamycin+IL-10 induced expansion and differentiation of type 1 T regulatory (Tr1) and $CD4^+CD25^+$ Tr cells, which mediate antigen-specific tolerance through different mechanisms including the production of suppressive cytokines (IL-10 and TGF-β), and inhibition of T cell activation.

Rapamycin+IL-10 combined preparations according to the invention exert a long term protection, which can be maintained after drug withdrawal despite recovery of T cell immunocompetence.

In a further embodiment the invention provides pharmaceutical compositions containing IL-10 and rapamycin and optionally further active ingredients selected from immunosuppressant or immunomodulating agents, monoclonal antibodies and cytokines, together with pharmaceutically acceptable excipients. Suitable pharmaceutical compositions are administered by the oral, intravenous, parenteral, or subcutaneous route, and are preferably in the form of solutions, suspensions, injectables, tablets, or capsules. Effective amounts of rapamycin may range from 0.001 mg/Kg to 100 mg/Kg and effective amounts of IL-10 may range from 0.001 µg/Kg to 1000 µg/Kg.

The invention is further illustrated by the following examples and the enclosed figures.

Balb/c mice that had been rendered diabetic by streptozotocin injection were transplanted under the kidney capsule with purified allogeneic C57BL/6 β-islets. Mice were not treated (control, n=13 mice), or treated with rapamycin+antiTac+IL-10 (IL-10 protocol, n=16 mice) or rapamycin+antiTac+FK506 (Edmonton protocol, n=4 mice) for 30 days. Graft survival was monitored by glycemia levels. A graft was considered rejected when glycemia was higher than 250 mg/dl.

Replacemnnt of FK506 (Edmonton protocol) with IL-10 (IL-10 protocol) resulted in comparable graft survival: in mice treated with the IL-10 protocol graft survival was 89% whereas 100% survival was observed in mice treated with the Edmonton protocol.

Figure 2:
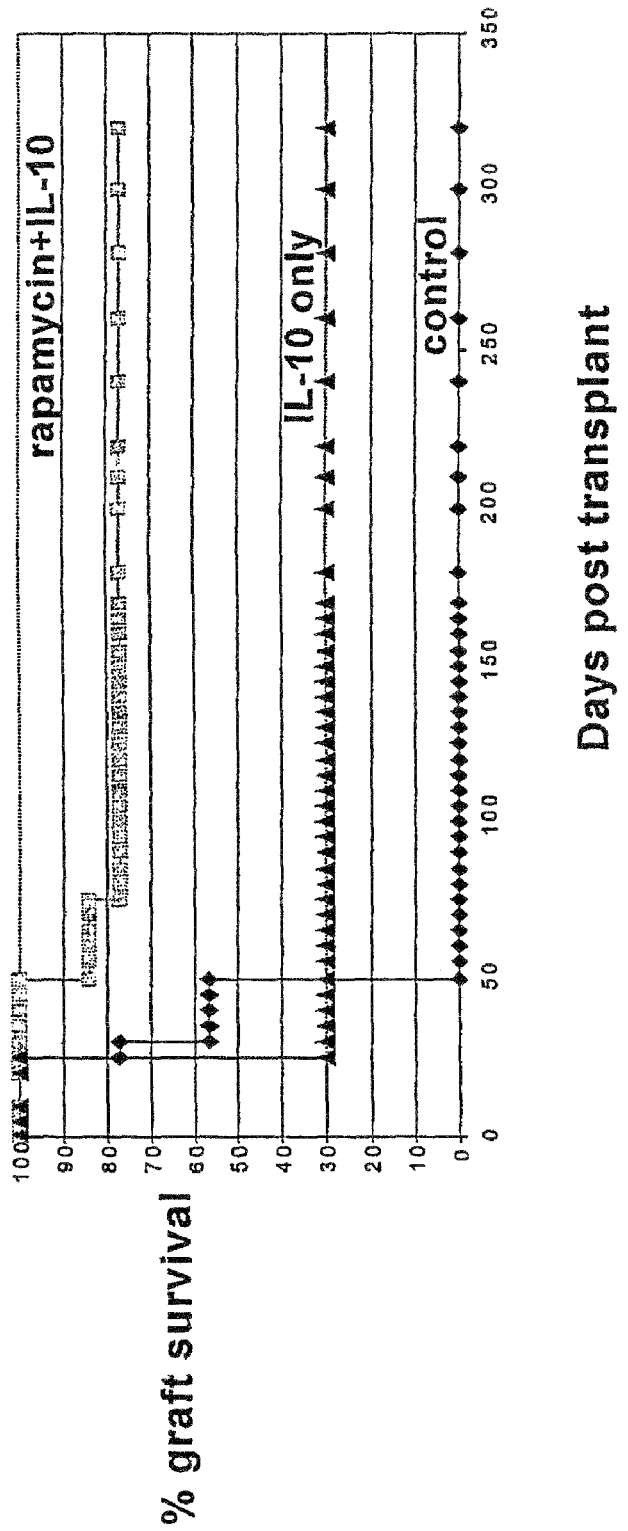

FIG. 2 The absence of antiTac from the IL-10 protocol slightly increases allogeneic β-islets rejection.

Balb/c mice that had been rendered diabetic by streptozotocin injection were transplanted under the kidney capsule with purified allogeneic C57BL/6 β-islets. Mice were not treated (control, n=8 mice), or treated with rapamycin in combination with IL-10 (rapa+IL10, n=8 mice) or IL10 only (n=4 mice). Graft survival was monitored by glycemia levels.

The absence of antiTac from the IL-10 protocol (see FIG. 1) slightly affected graft survival. Rapamycin in combination with IL-10 allowed graft survival in 78% of the animals. Treatment with IL-10 alone was not efficient in preventing graft rejection.

These data suggest that the antiTac is not required to prevent allograft rejection.

Figure 3:
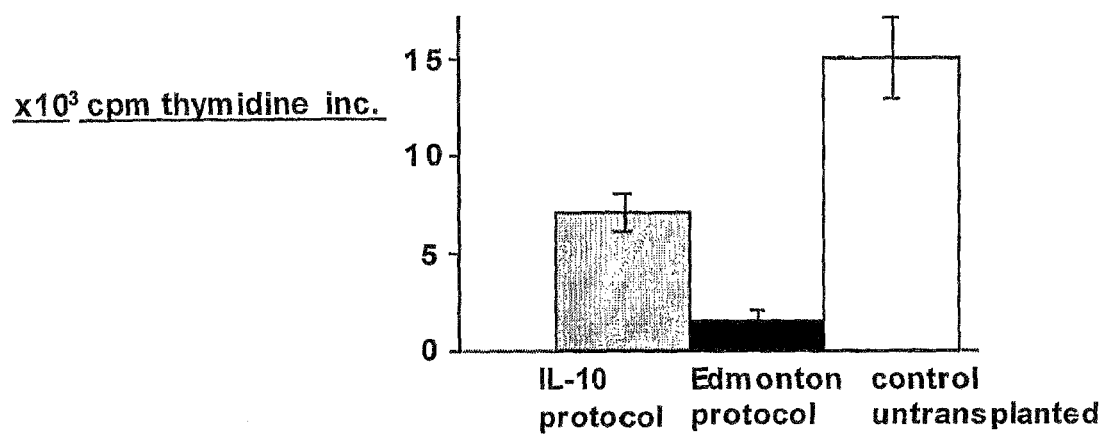

FIG. 3 T cells from mice treated with the IL-10 protocol maintain an in vitro proliferative capacity.

T cells from control untransplanted mice (white bars) and mice treated with the IL-10 protocol (gray bars), or the Edmonton protocol (black bars) were isolated from the spleen and stimulated in vitro polyclonally with antiCD3 and antiCD28 mAbs. Cells from mice treated with the Edmonton protocol were strongly reduced in their in vitro proliferative capacity while only a mild reduction in proliferation was observed in T cells isolated from mice treated with the IL-10 protocol.

These data suggest a profound state of immunosuppression in T cells isolated from mice treated with the Edmonton protocol but not from mice treated with the IL-10 protocol.

Figure 4:
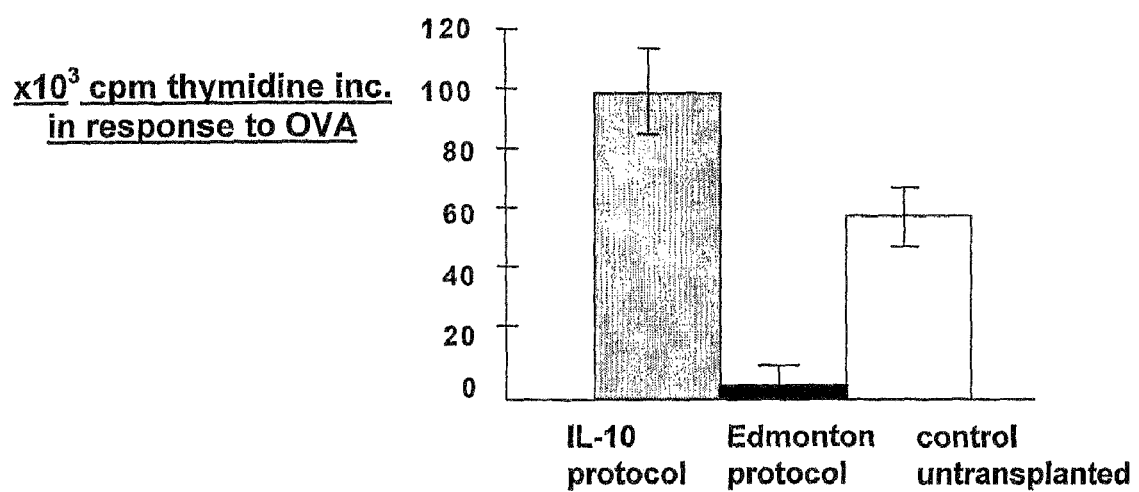

FIG. 4 T cells from mice treated with the IL-10 protocol preserve an antigen-specific proliferative capacity.

Mice transplanted 280 days before and treated only for 30 days with the IL-10 protocol (gray bars), or the Edmonton protocol (black bars), were immunized in vivo in the hind foot pad with CFA+OVA. Draining lymph nodes were collected and re-stimulated in vitro with OVA and self APC.

OVA-specific T cell proliferation was strongly reduced in mice treated with the Edmonton protocol while OVA-responce in mice treated with the IL-10 protocol was comparable to that observed in untransplanted immunized mice.

Figure 5:
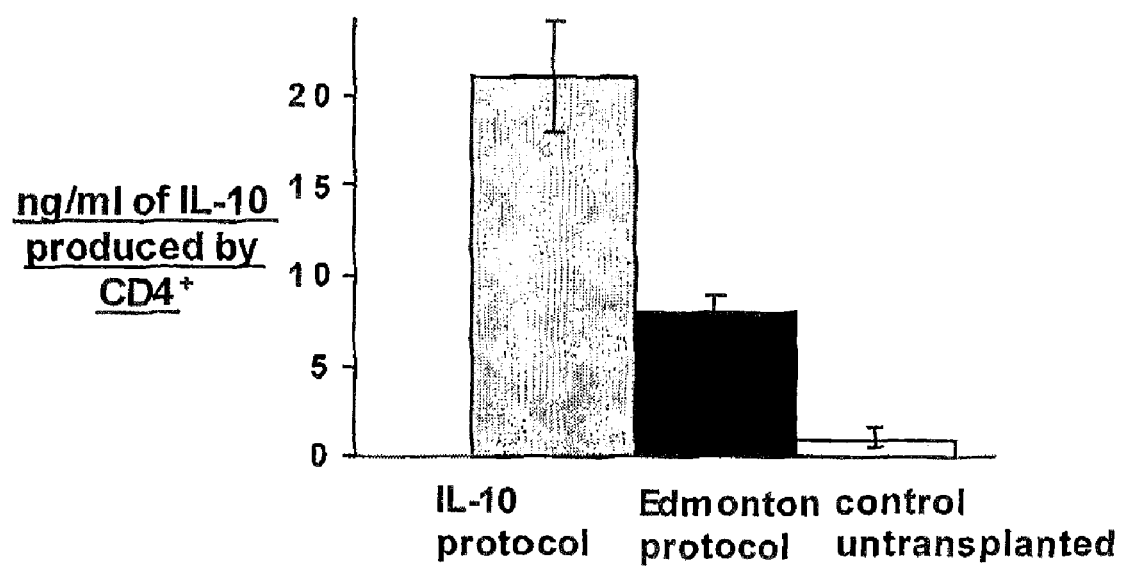

These data further demonstrate a general state of immunosuppression in mice treated with the Edmonton protocol, but not with the IL-10 protocol FIG. 5 T cells isolated from mice treated with the IL-10 protocol produce IL-10.

$CD4^+$ T cells isolated from the kidney of control untransplanted mice or mice treated with the IL-10 protocol (gray bars) and the Edmonton protocol (black bars) were stimulated in vitro with antiCD3 and antiCD28 mAbs. Supernatants were collected 96 hours after stimulation and IL-10 production was evaluated by ELISA.

Figure 6:
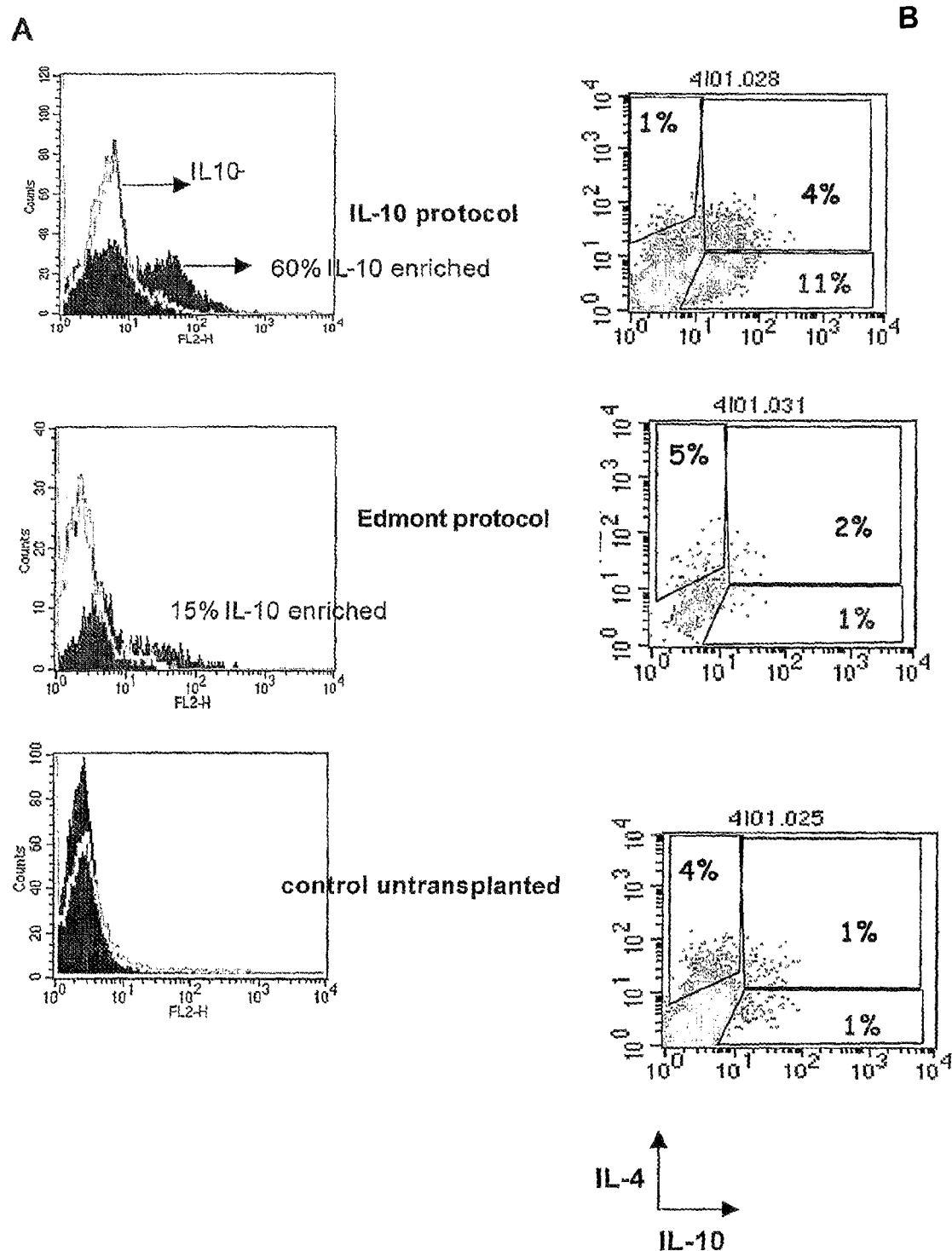

T cells from mice treated with the IL-10 protocol produced higher levels of IL-10 compared to mice treated with the Edmonton protocol and control untransplanted mice FIG. 6 A distinct population of IL-10 producing T cells can be isolated from mice treated with the IL-10 protocol.

(A) T cells from mice treated with IL-10 protocol, Edmonton protocol, and from control untransplanted mice were isolated and stimulated polyclonally in vitro to induce cytokine production. After 3 hours, the cells were labeled with a diabody consisting of one mAb that binds an ubiquitous cell surface marker and the other mAb able to catch IL-10. The labeled cells were then incubated for an additional hour at 37° C. in order to release cytokines accumulated during polyclonal stimulation. IL-10 produced by the labeled cells was captured by the diabody. Cells were further labeled with an antiIL-10 mAb labeled with PE. Anti-PE microbeads were used in order to magnetically separate IL-$10^+$ enriched (filled histogram) and $IL10^-$ (empty histogram) cells. A distinct population of IL-10+ enriched T cells was isolated only from transplanted mice treated with the IL-10 protocol.

(B). Intracytoplasmic staining was performed on this distinct IL-$10^+$ enriched T cell population and a significant proportion of cells with a Tr1 cytokine profile (i.e. IL-$10^+$,IL-$4^-$) was identified in mice treated with the IL-10 protocol but not in mice treated with the Edmonton protocol or control untransplanted mice FIG. 7 IL-10 is required to induce IL-10 producing T cells in vivo.

To understand the requirement for IL-10 administration to induce IL-$10^+$ Tr1 cells in vivo, transplanted mice were treated with the IL-10 protocol (rapamycin+antiTac+IL-10)

or rapamycin+antiTac only. The production of IL-10 by CD4+ splenic T cells in the two groups of mice was then evaluated.

T cells from mice treated with the IL-10 protocol (gray bars), or rapamycin+antiTac (black bars), or control untransplanted (white bars) were isolated and stimulated in vitro polyclonally with antiCD3 and antiCD28 mAbs.

Significant levels of IL-10 were produced only by cells isolated from the IL-10 protocol treated mice.

These data suggest that IL-10 is required in order to induce IL-10 producing cells in vivo.

Figure 8:
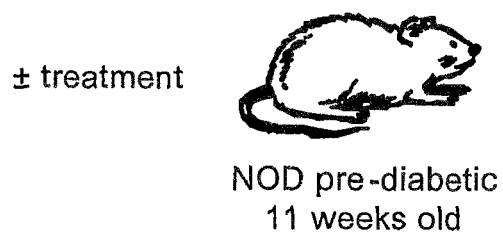

FIG. 8 Preliminary results with rapamycin+IL-10 for the treatment of type I diabetes in NOD mice.

(A) NOD mice at 11 weeks of age are at a stage of pre-diabetes. These mice have insulitis and infiltrating autoimmune T cells in the pancreas, however they still have enough normal β-islets left able to produce sufficient insulin to be normoglycemic.

(B) Pre-diabetic mice were treated daily starting from 11 weeks of age with either rapamycin, rapamycin+IL-10 or IL-10 alone. Six weeks after treatment, 33% of control mice developed diabetes while mice treated with rapamycin and IL-10 are still all normoglycemic.

These preliminary results suggest that rapamycin+IL-10 can be used to block diabetes in its early stage and to prevent the further spontaneous development of full blown autoimmune diabetes.

Figure 9:
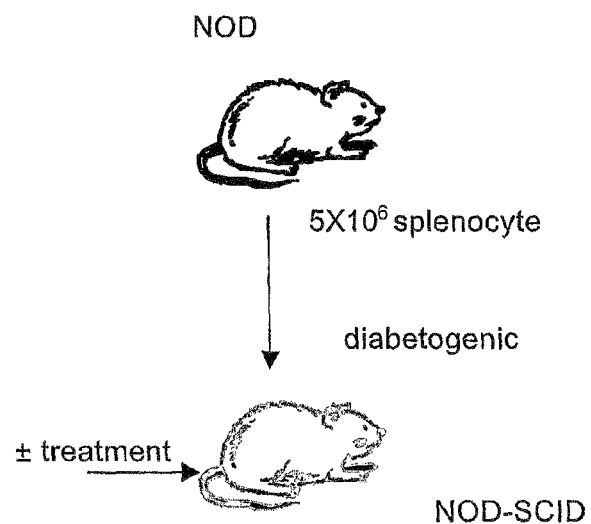

FIG. 9 The IL-10 protocol inhibits diabetes induced in NOD.SCID mice following transfer of diabetogenic T cells.

(A) 5×10$^6$ splenocytes from NOD diabetic mice were transferred intravenously in NOD.SCID mice. The recipient mice were either untreated or treated with the Edmonton protocol (rapamycin+antiTac+FK506), IL-10 protocol (rapamycin+antiTac+IL-10), or rapamycin+antiTac for 40 days after transfer.

Fifty days post transfer all the control untreated mice were diabetic.

(B) All the mice treated with the Edmonton protocol and 75% of the mice treated with rapamycin+antiTac became diabetic. Interestingly, only 33% of the mice treated with the IL-10 protocol became diabetic.

These preliminary data indicate that the IL-10 protocol inhibits type I diabetes induced in NOD.SCID mice by transferring autoimmune diabetogenic NOD T cells.

Figure 10:
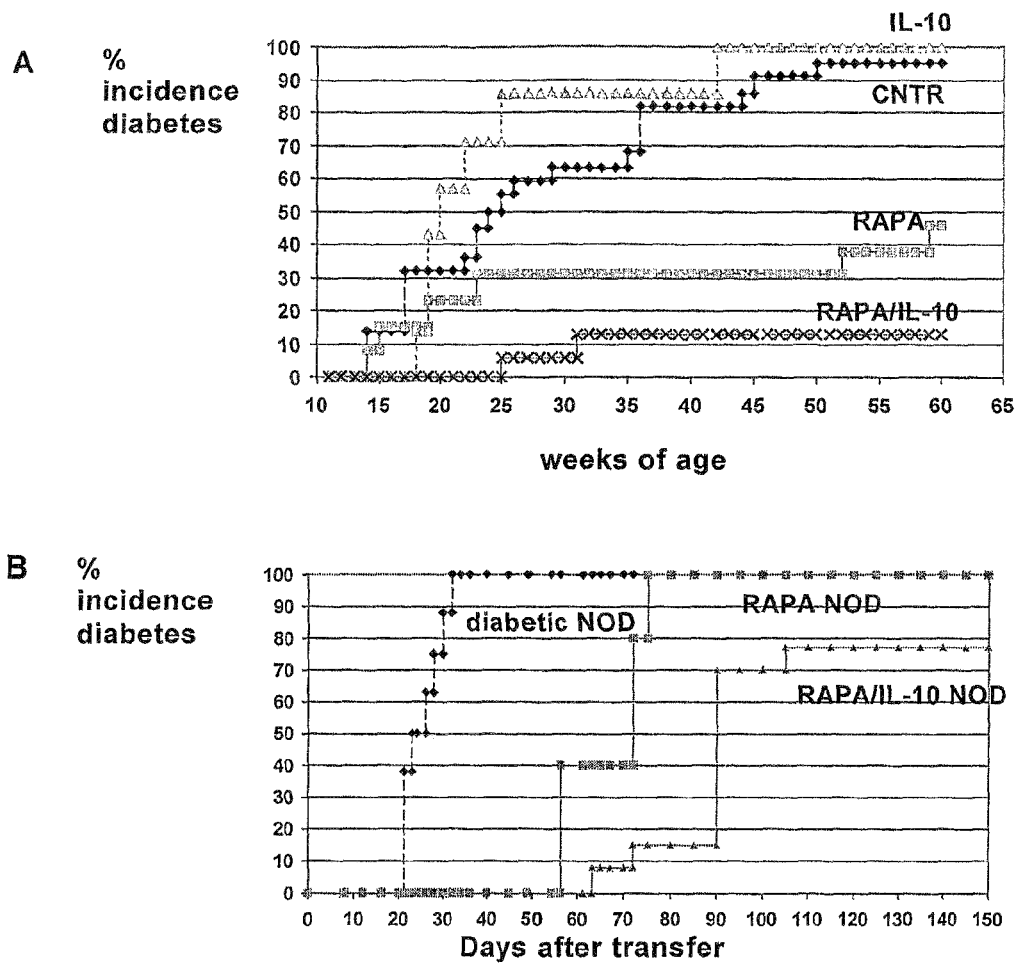

FIG. 10 Use of Rapamycin+IL-10 for Treatment of Type I Diabetes.

A) Treatment of diabetes in NOD mice.

NOD mice were treated from 11 weeks to 31 weeks of age with IL-10 (IL-10, n=7 mice), or rapamycin (RAPA, n=13 mice), or rapamycin+IL-10 (RAPA/IL-10 n=16 mice), or vehicle (CNTR, n=22 mice). Diabetes incidence, monitored by glycemia levels, was stable at least up to 60 weeks of age. Administration of rapamycin alone reduced diabetes incidence from 95% to 46%. IL-10 administration had no significant effect on the development of diabetes. The protective effect of rapamycin was significantly improved when IL-10 was added to the treatment reducing diabetes incidence to 13%.

B) Ability of splenocytes from treated NOD mice to transfer diabetes in NOD.SCID mice.

5×10$^6$ total splenocytes from untreated-diabetic NOD mice (DIABETIC NOD n=8) or mice treated with rapamycin (RAPA NOD, n=5) or rapamycin+IL-10 (RAPA/IL-10 NOD n=13) were transferred in NOD.SCID mice and diabetes incidence was monitored by glycemia levels.

Transfer of splenocytes from rapamycin-treated mice resulted in a significant delay in onset of the disease, compared to mice injected with splenocytes from diabetic NOD mice. Importantly, splenocytes from mice treated with rapamycin+IL-10 even further delayed diabetes transfer.

Figure 11:
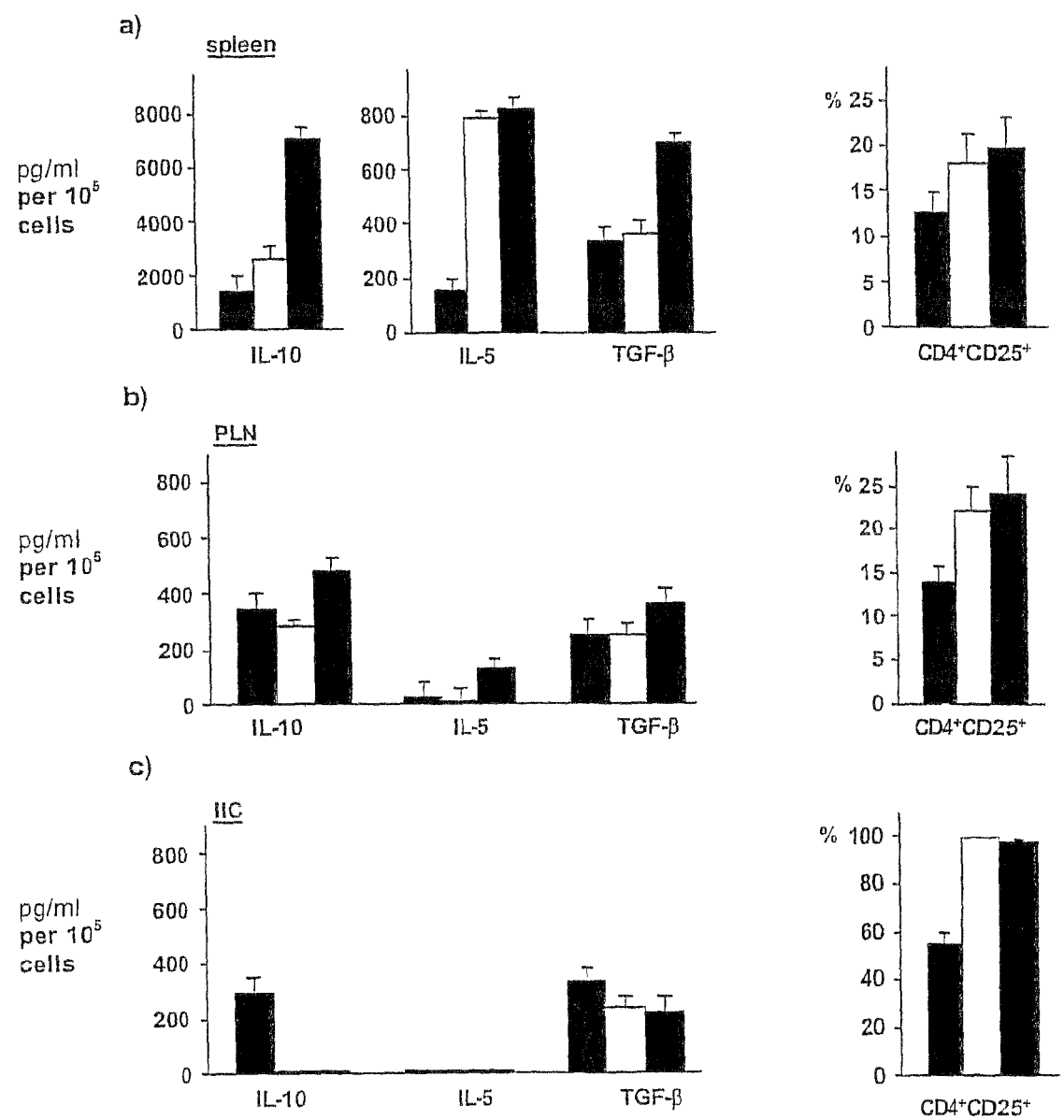

FIG. 11 Tr cells content in mice treated with rapamycin±IL-10.

Cytokine production by CD4+ T cells (left panels) and percentages of CD4+CD25+ T cells (right panels) were evaluated by CBA and FACS analysis respectively, in the spleen (A), pancreatic lymph nodes (PLN) (B), and islet infiltrating cells (IIC) (C) of untreated-diabetic NOD mice (gray bars), rapamycin-treated mice (white bars), or rapamycin+IL-10-treated mice (black bars). A high proportion of CD4+ Tr1 cells, as determined by their cytokine production profile (i.e. IL-10++ IL-15+ TGF-β+), was present only in spleens of tolerant mice treated with rapamycin+IL-10 (black bars). The percentages of CD4+CD25+ T cells were higher in the spleen, PLN, and IIC of both mice treated with rapamycin alone or rapamycin+IL-10 (black bars). Therefore, in rapamycin+IL-10 treated mice, Tr1 cells are present in the spleen and CD4+CD25+ Tr cells are present in the spleen, lymph nodes, and pancreas.

Figure 12:
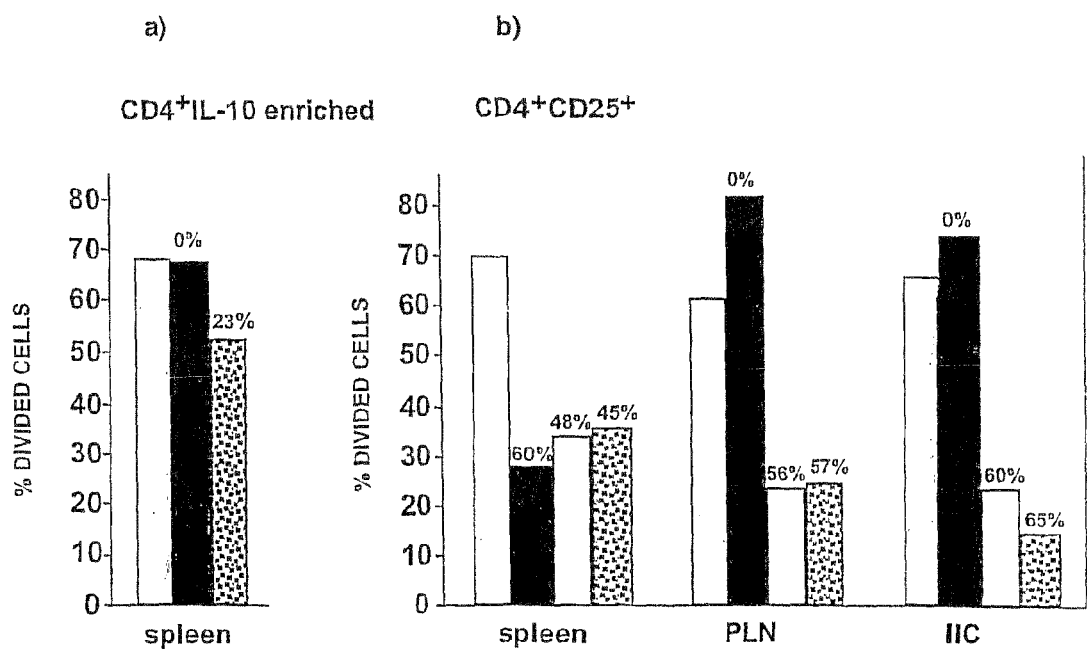

FIG. 12 Ability of Tr cells to suppress immune responses in vitro.

In vitro suppressive activity of Tr cells on proliferation of CD4+ naïve NOD T cells labeled with CFSE and cultured in the presence of antiCD3 mAb was tested. Either CD4+ IL-10 enriched splenic T cells (purity ~40%) (A) or CD4+CD25+ T cells (MACs purified, purity≧75%) (B) were used as suppressor cells added in equal number to naïve T cells. Naive T cells divided in the absence of any added cells (gray bars) were used as control. Cell division in the presence of CD4+ IL-10 enriched Tr1 cells or CD4+CD25+ Tr cells isolated from untreated-diabetic NOD mice (black bars), or rapamycin-treated mice (white bars), or rapamycin+IL-10-treated mice (dotted bars) was evaluated and percentages of suppression relative to control were determined (numbers on top of each histogram). Tr1 cells from spleens of rapamycin+IL-10 treated mice mildly suppress the proliferative responses of CD4+ T cells obtained from NOD mice. Strong suppression was observed with CD4+CD25+ T cells isolated from PLN and IIC of both rapamycin and rapamycin+IL-10 treated mice.

EXAMPLES

Example 1

1. Allogeneic β-islet transplantation. A model of fully mismatched murine islet allotransplantation (C57BL/6 into Balb/C) was used. Allogeneic pancreatic β-islet transplantation is becoming a valid alternative to insulin replacement therapy or to pancreas transplantation for the cure of type 1 diabetes. In the past years improved methods for the isolation and preservation of human β-cells and development of new immunosuppressive agents have significantly improved the clinical outcome of these transplants. Specifically, a new steroid-free immunosuppressive regimen based on rapamycin+antiTac+FK506 (the Edmonton protocol) has been recently shown to induce insulin independence in 80% of the patients at 1 year after transplant (Shapiro et al. 2000). These results largely exceed the ones obtained with all previous immunosuppressive combination therapies. However, the demonstration that this regimen may induce tolerance has not been produced. Importantly, the mechanism of action of FK506 might prevent a state of tolerance induction due to prevention of apoptosis and inhibition of Tr cells development In an effort to develop a tolerogenic protocol we designed a regimen in which FK506 in the Edmonton protocol was replaced by IL-10 (i.e. IL-10 protocol: rapamycin+antiTac+ IL-10).

Figure 1:
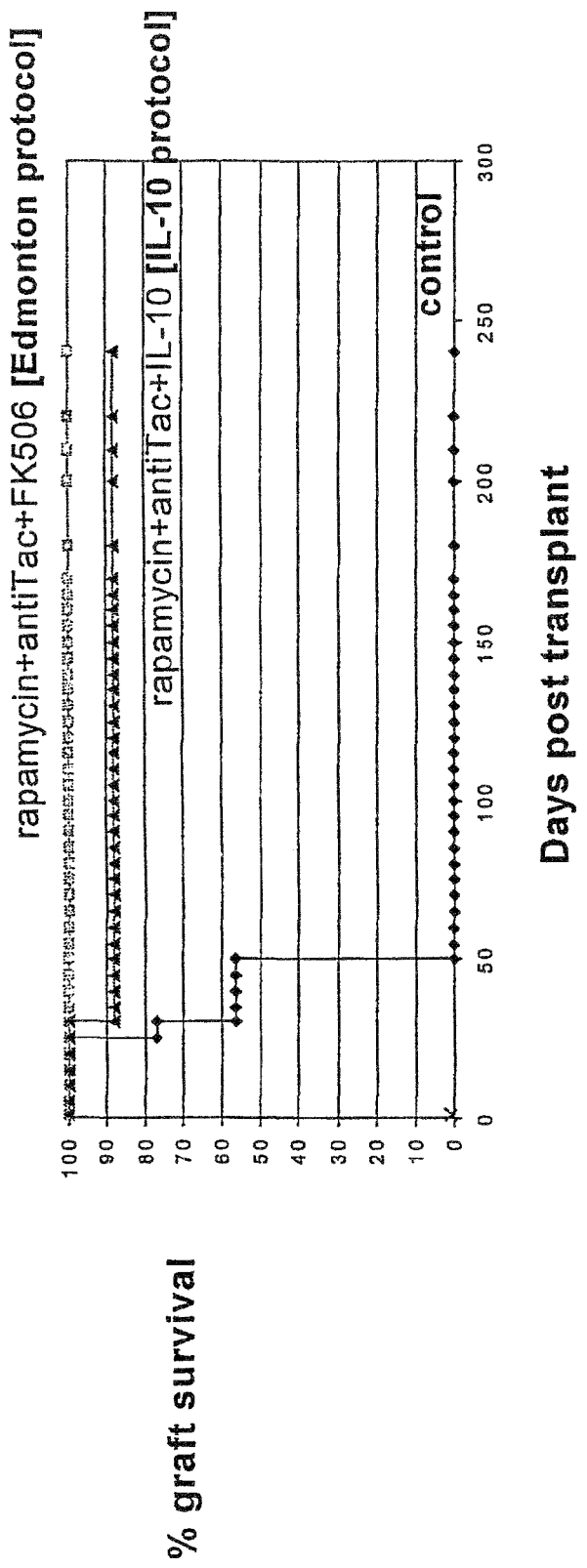
FIG. 1 Mice treated with the IL-10 protocol and the Edmonton protocol have comparable graft survival.

Balb/c mice that had been rendered diabetic by streptozotocin injection were transplanted under the kidney capsule with purified allogeneic C57BL/6 β-islets. Graft survival was similar (89% and 100% at 240 days post transplant) in mice treated with the IL-10 protocol and the Edmonton protocol, respectively (FIG. 1).

The in vivo usage of antiTac has been strongly supported in the past years by the need to block activated T cells with high IL2Rα chain expression. However, it has been widely demonstrated that a subset of Tr cells constitutively express the IL2Rα chain (i.e. $CD4^+CD25^+$ Tr cells) and that this T cell population is able to suppress allograft rejection (Taylor et al. 2002). Therefore, the usage of a mAb which blocks the $CD25^+$ T cell population might be counterindicated when in vivo tolerance induction mediated by Tr cells is sought. For this reason, removal of antiTac from the treatment protocol was evaluated. We treated transplanted mice for 30 days with rapamycin+IL-10 or IL-10 alone in order to determine whether it would be sufficient to prevent islet rejection (FIG. 2). Long-term graft survival was obtained in 30% of the mice treated with IL-10 alone and it increased to 78% in mice treated with rapamycin+IL-10. This level of graft survival was only slightly lower than that of mice that in addition were treated with antiTac (as shown in FIG. 1). These data indicate that the absence of antiTac mAb from the IL-10 protocol allows allograft survival while $CD4^+CD25^+$ Tr cells are not affected and in vivo tolerance induction by these cells could be preserved.

Since one of the desired outcomes is tolerance rather than immunosuppression, we examined whether T cells from mice treated with IL-10 and Edmonton protocols were responsive to polyclonal and antigen specific stimulation. First, T cells were isolated from spleens of mice at day 240 after transplantation (210 days after cessation of treatment) and stimulated with antiCD3 and antiCD28 mabs (FIG. 3). Proliferation of T cells from mice treated with the Edmonton protocol was strongly suppressed when compared to that of T cells from control untransplanted mice. Suppression of T cell proliferation was not as strong in mice treated with the IL-10 protocol (FIG. 3). Next, 280 days post transplant (250 days after cessation of treatment) mice were immunised with CFA plus OVA in the hind foot pad and proliferative responses of T cells isolated from the draining lymph nodes was measured (FIG. 4). T cells from mice treated with the Edmonton protocol did not proliferate in response to OVA, whereas T cells from mice treated with the IL-10 protocol had similar responses as untransplanted immunised control mice (FIG. 4).

In order to determine whether the replacement of FK506 by IL-10 potentially promoted Tr1 cell expansion, $CD4^+$ T cells infiltrating the site of islet transplantation were isolated from mice 200 days after transplant and their cytokine production was examined. $CD4^+$ T cells isolated from mice treated with the IL-10 protocol produced significantly higher amounts of IL-10 after stimulation with antiCD3 and antiCD28 mAbs than mice treated with the Edmonton protocol (FIG. 5). Purified spleen T cells were then stimulated with antiCD3 and antiCD28 mAbs and the IL-10 secreting cells were enriched using IL-10 capture beads (FIG. 6A). The IL-10/IL-4 cytokine profile was examined by intracytoplasmic staining (FIG. 6B). Interestingly, a distinct population of $IL10^+IL4^-$ cells (i.e. reflecting the cytokine profile of Tr1 cells) was identified only in mice treated with the IL-10 protocol.

Figure 7:
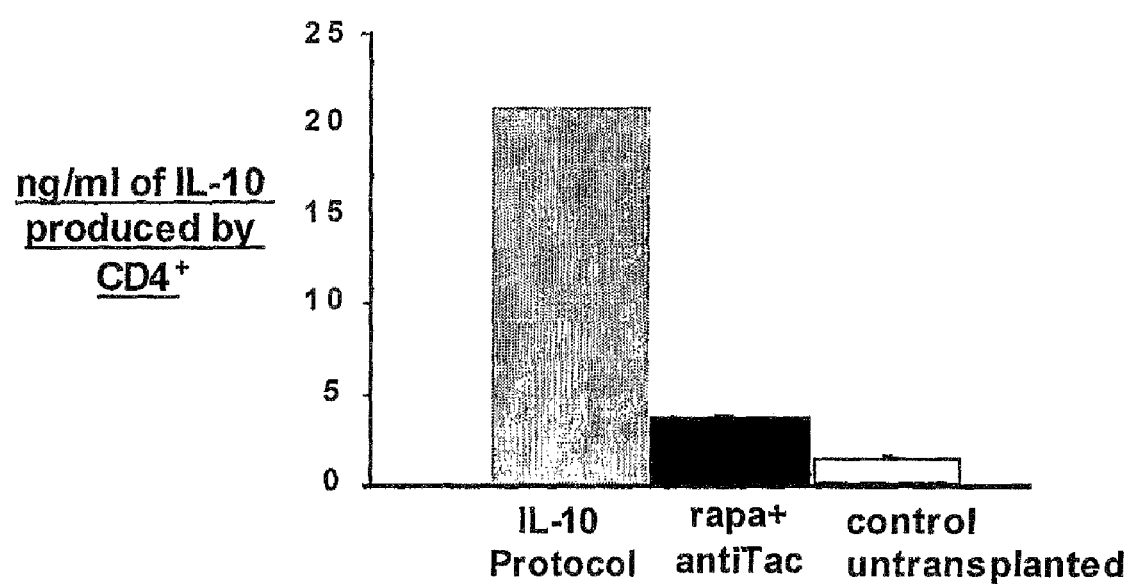

Infiltrating cells from mice treated with rapamycin+antiTac in the absence of IL-10 did not produce IL-10, indicating that increased in vitro IL-10 production was due to the in vivo administration of IL-10 (FIG. 7).

Collectively, these data indicate that:
1. The combination of rapamycin+antiTac+FK506 (Edmonton protocol) protects mice from allo-rejection but induces a state of long-lasting chronic immunosuppression.
2. The combination of rapamycin+antiTac+IL-10 (IL-10 protocol) provides long-term protection against allo-rejection. This treatment results in expansion of a distinct population of T cells with cytokine profiles consistent with Tr1 cells and protection is maintained after drug withdrawal despite recovery of T cell immunocompetence.

Example 2

1. Preliminary results in type I diabetes. The tolerogenic effect of rapamycin+IL-10 was also evaluated in a setting of type I diabetes.

We believe that prevention of β-cell destruction, which is associated with progression to type I diabetes and is found at disease onset, can be prevented by:
1. Down-regulation of the general 'bystander' inflammation within the pancreas.
2. Blockade of the expansion of islet specific T effector cells.
3. Induction and expansion of antigen-specific Tr cells.

In our proposed protocol, down-regulation of inflammation should be achieved by IL-10, and blockade of T effector cell expansion should be achieved by rapamycin. Neither IL-10 nor rapamycin prevent T cell priming and therefore they should allow induction of antigen-specific T regulatory cells, and as described below, IL-10 should promote the induction and expansion of Tr1 cells. We investigated the effect of rapamycin alone or in combination with IL-10 in treating autoimmunity in the NOD mouse a model for type I diabetes. The NOD mouse develops overt disease at 15-30 weeks of age with destruction of the β-cells of the islets and elevations in blood glucose and shares many key features with the human disease (Tisch et al. 1996, Delovitch et al. 1997). Inhibition of type I diabetes was evaluated by treating NOD mice daily starting at 11 weeks of age (i.e. pre-diabetic mice with periinsultis) with rapamycin, rapamycin+IL-10, or IL-10 alone. Six weeks after treatment, 33% of untreated control mice started developing diabetes while mice treated with rapamycin+IL-10 are still all normoglycemic (FIG. 8).

The efficacy of our protocol was also tested in a model of adoptive transfer. NOD.SCID mice, which lack endogenous T and B cells and therefore do not develop diabetes spontaneously, develop diabetes in 15-20 days after transfer of $5 \times 10^6$ splenocytes from a diabetic NOD mouse. NOD.SCID recipient mice were either untreated or treated for 40 days after transfer of diabetic cells with rapamycin+antiTac+ FK506 (Edmonton protocol), rapamycin+antiTac+IL-10 (IL-10 protocol), and rapamycin+antiTac (FIG. 9). Control mice started developing diabetes 15 days after transfer. All the mice treated with the Edmonton protocol and 75% of the mice treated with rapamycin+antiTac became diabetic within 33 days after transfer. Interestingly, only one mouse out of three treated with the IL-10 protocol (33%) became diabetic 35 days after transfer.

All together these preliminary data provide strong rationale for the use of rapamycin+IL-10 to inhibit full development of type I diabetes.

2. Rapamycin+IL-10 therapy inhibits autoimmune diabetes and induces long-term tolerance. Based on the promising preliminary results obtained in the NOD mouse model (FIG.

8) we treated NOD mice for 20 weeks with rapamycin±IL-10 starting at 11 weeks of age, a time point at which pancreatic-cell autoimmunity is clearly established as judged by insulitis and auto-insulin antibodies. Administration of rapamycin alone reduced the incidence of diabetes from 95% to 46% (FIG. 10A). Previous observations indicated that the effects of IL-10 therapy in NOD mice vary depending on route, dose, and timing of administration (Roncarolo et al. 2003). However, here we show that administration of IL-10 alone over the same time period had no significant effect on the development of diabetes. The protective effect of rapamycin was significantly improved when IL-10 was added to the treatment, further reducing the incidence of diabetes to 13% (FIG. 10A). Interestinggly, protection was maintained for an additional 30 weeks after the treatment was stopped, demonstrating establishment of long-term immunomodulation.

The mechanism by which rapamycin or rapamycin+IL-10 prevents development of autoimmune diabetes was further investigated in transfer experiments with cells from tolerant mice. Transfer of splenocytes from untreated-diabetic NOD mice in inmunodeficient NOD.SCID mice rapidly induced diabetes, while transfer of splenocytes from rapamycin-treated mice resulted in a significant delay in onset of the disease. Interestingly, transfer of splenocytes from mice treated with the combination of rapamycin+IL-10 even further delayed diabetes transfer (FIG. 10B). These data indicate that treatment with rapamycin down-regulates the ability of splenic autoreactive T cells to transfer diabetes and that this effect is strongly enhanced when IL-10 is added to the treatment.

The mechanisms underlying long-term tolerance were analysed in tolerant mice of 50 weeks of age or older. Although spleens from untreated-diabetic NOD mice or rapamycin±IL-10-treated mice contained comparable cell numbers and the same proportion of $CD4^+$ and $CD8^+$ T cells, their cytokine production profiles were distinct. A high proportion of $CD4^+$ Tr1 cells, as determined by their cytokine production profile (i.e. $IL-10^{++}IL-5^+TGF-\beta^+$), was present in spleens of tolerant mice treated with rapamycin+IL-10, but not in spleen of mice treated with rapamycin alone or untreated-diabetic NOD mice (FIG. 11). However, the proportion of splenic $CD4^+$ T cells producing IL-4 was the same in both untreated and treated mice. In addition, the percentages of splenic $CD4^+CD25^+$ T cells were higher in both mice treated with rapamycin alone or rapamycin+IL-10, as compared to untreated-diabetic NOD mice (FIG. 11). In contrast, no Tr1 cells could be detected in pancreatic lymph nodes (PLN) and islet infiltrating cells (IIC) (FIG. 11), indicating that Tr1 cells are not present at the site of autoimmunity. On the other hand, $CD4^+CD25^+$ T cells were observed in high numbers in PLN, and represented almost 100% of the $CD4^+$ T cells isolated from the IIC of mice treated with either rapamycin alone or rapamycin+IL-10 but not in untreated-diabetic mice (FIG. 11). These $CD4^+CD25^+$ T cells from IIC were anergic and did not produce significant levels of cytokines with the exception of $TGF-\beta$.

Next we determined whether the Tr1 cells present in spleens of rapamycin+IL-10 treated mice and the $CD4^+CD25^+$ T cells from spleens, PLN, and IIC of rapamycin and rapamycin+IL-10 treated mice had suppressive activity in vitro. Tr1 cells from spleens of rapamycin+IL-10 treated mice mildly suppressed the proliferative responses of $CD4^+$ T cells obtained from NOD mice (FIG. 12). Suppression was also observed with $CD4^+CD25^+$ T cells purified from spleens of both treated and untreated-diabetic NOD mice (FIG. 12), which indicates that $CD4^+CD25^+$ Tr cells are also present in spleens of diabetic NOD mice, but at much lower frequencies (shown in FIG. 11). Interestingly, strong suppression was observed with $CD4^+CD25^+$ T cells isolated from PLN and IIC of both rapamycin or rapamycin+IL-10 treated mice. In contrast, $CD4^+CD25^+$ T cells isolated from untreated-diabetic NOD mice did not have any measurable suppressive activity (FIG. 12). These data indicate that pancreatic tissue of diabetic NOD mostly contain activated Teff cells rather than Tr cells, whereas PLN and IIC of treated mice contain predominantly Tr cells among the $CD4^+CD25^+$ subset.

Overall, these data show that the steady-state tolerance observed following rapamycin+IL-10 treatment is associated with accumulation of Tr1 cells in the spleen and of $CD4^+CD25^+$ Tr cells in the lymph nodes and pancreas.

Materials and Methods

Mice. Balb/c, C57BL/6, NOD/Lt, and NOD.SCID female mice were purchased from Charles River Laboratories (Calco, Italy). All mice were kept under specific pathogen free conditions. Glucose level in the tail venous blood was quantified using Glucometer Elite system (Bayer, Wuppertal, Germany). Diabetes was induced in Balb/c mice by intravenous injection of streptozotocin (Sigma, St. Louis, Mo.) at 170 mg/kg. A diagnosis of diabetes was made after two sequential glucose measurements higher than 250 mg/dl.

Islet transplant. Hand picked C57BL/6 pancreatic islets were transplanted (300 islets/mouse), after overnight cultures at 37° C., under the kidney capsule of Balb/c diabetic mice as previously described (Davalli et al. 1996).

Treatment of transplanted mice. Treatment of transplanted Balb/c mice began the day after transplant and lasted for 30 days. Rapamycin (Rapamune, Wyeth-Ayerst Research, Pearl River, N.Y.) was diluted in peanut oil (Sigma) and administered once daily at a dose of 1 mg/kg by gavage. Human IL-10 (BD Biosciences, Mountain View, Calif.) was diluted in PBS and administered twice a day at a dose of 0.05 mg/Kg IP. FK506 (Prograf, Fujisawa, Milano) was diluted in saline solution and administered once daily at a dose of 0.3 mg/kg IP. AntiIL-2Rα chain mAb (antiTac) (clone 7D4, BD) was diluted in saline solution and administered IP at time 0 and 4 days post transplant to reach a final dose of 1 mg/mouse. Diabetes incidence was monitored by blood glucose levels.

Diabetes inhibition study. Female NOD mice were treated from age 11 weeks to 31 weeks of age with rapamycin, rapamycin+IL10, or IL-10 alone at the same doses used in transplanted mice. Diabetes incidence was monitored by blood glucose levels.

Diabetes transfer study. Splenocytes from diabetic NOD female mice were collected and injected IV in NOD.SCID at a dose of $5 \times 10^6$ per mouse. Recipient mice were untreated or treated with rapamycin+antiTac+FK506, or rapamycin+antiTac+IL-10, or rapamycin+antiTac for 40 days after transfer at the same doses used in transplanted mice. Diabetes incidence was monitored by blood glucose levels.

Adoptive cell transfer in NOD.SCID mice. Spleens from control and treated NOD mice were collected after stopping the treatment. Five millions total splenocytes were adoptively transferred by IV injection into NOD.SCID mice. Diabetes development was monitored by glucose levels.

In vivo immunisation. Ovalbumin (OVA) peptide 323-339 (Primm, Milano, Italy) emulsified in CFA (Difco, Detroit, Mich.) was injected at a dose of 100 μg/mouse once S.C. in the hind footpads of transplanted Balb/c mice. Draining lymph nodes were collected and used in the in vitro assays.

Cell sorting. The cells infiltrating the pancreas were isolated as described (Gregori et al., 2003). The obtained cell population was incubated with antiCD90 mAb-coated microbeads and applied onto MiniMacs columns (Miltenyi Biotec, Bergisch Gladbach, Germany) to obtain purified T cells.

CD4⁺CD25⁺ T cells were sorted with a Multisort kit (Miltenyi) (average purity≧75%). In some experiment CD4⁺CD25⁺ T cells were sorted aseptically on a FACStar cell sorter (BD) (average purity=99%). IL-10 producing cells were sorted with the murine IL-10 secretion assay enrichment and detection kit (Miltenyi) (average purity≧40%).

Enrichment of IL-10 positive cells. IL-10 producing cells were enriched by means of a commercially available kit (Miltenyi). Purified T cells were cultured at a concentration of $10^6$/ml in the presence of immobilised antiCD3 and soluble antiCD28. After 3 hours of culture, cells were harvested and labeled for 10 minutes at 4° C. with a diabody consisting in a mAb directed against CD45 and another mAb capturing murine IL-10. The cells were then diluted at a final concentration of $10^5$n/ml and allowed to secrete cytokines for 45 minutes at 37° C. After the cytokine capture period, cells were harvested, resuspended $10^8$/ml in PBS containing 0.5% BSA and 5 nM EDTA (buffer) and stained for 10 min. at 4° C. with PE-conjugated αIL10 mAb (BD). Cells were washed in buffer once, resuspended $10^8$/ml and stained with anti-PE microbeads for 10 min at 4° C. IL-10 enriched cell population was isolated on magnetic columns. Cell samples were analysed on a FACScalibur flow cytometry (BD).

Cell cultures. For suppression experiments, naïve CD4⁺ NOD T cells were stained with CFSE (Molecular Probes, Eugene. Oreg.) as described elsewhere (Lyons et al. 1994) and cultured in 96 well plates ($\times 10^5$/well) in the presence of 10 µg/ml antiCD3 mAb (BD). CD4⁺ T cells obtained from NOD mice treated for 20 weeks with rapamycin, or rapamycin+IL-10 were added in 1:1 ratio to the culture and percentage of divided naïve cells was evaluated and compared to percentage of divided cells in the absence of any added cells. The divided cells were evaluated by dividing the events contained in the proliferating population by the total events CFSE⁺.

For measurement of cytokines released in the media, purified T cells ($1 \times 10^5$/well) were cultured in 96 well plates stimulated with 10 µg/ml immobilized antiCD3 (BD) and 1 µg/ml soluble antiCD28 (BD). Supernatants were collected after 48 (for IL-5 detection), and 96 hours (for IL-10 and TGF-β detection) of culture.

Flow cytometry. Cells were stained with the indicated Abs (all from BD), and were analyzed with a FACScan flow cytometer equipped with CellQuest software (BD).

Cytokine measurement. Cytokines present in the collected supernatants were quantified by sandwich ELISA or flow cytometry based assay (CBA), using standard commercially available kits (BD). The percentage of cells producing specific cytokines was measured by intracellular staining. Purified T cells were stimulated for 6 hours with 10 µg/ml immobilised antiCD3 and 1 µg/ml soluble antiCD28 (BD) at a concentration of $1 \times 10^6$/ml. Brefeldin A was added for the final 3 hours of culture. Intracellular staining was performed as previously described (Trembleau et al. 2000).

References

Bacchetta, R., M. Bigler, et al. (1994). "High levels of interleukin 10 production in vivo are associated with tolerance in SCID patients transplanted with HLA mismatched hematopoietic stem cells. Growth and expansion of human T regulatory type 1 cells are independent from TCR activation but require exogenous cytokines." Journal of Experimental Medicine 179(2): 493-502.

Bacchetta R., Parkman R., et al. (1995) "Dysfunctional cytokine production by host-reactive T-cell clones isolated from a chimeric severe combined immunodeficiency patient transplanted with haploidentical bone marrow." Blood 85: 1944-1953.

Baker, K. S., M. G. Roncarolo, et al. (1999). "High spontaneous IL-10 production in unrelated bone marrow transplant recipients is associated with fewer transplant-related complications and early deaths." Bone Marrow Transplant 23(11): 1123-9.

Battaglia, M., B. R. Blazar, et al. (2002). "The puzzling world of murine T regulatory cells." Microbes Infect 4(5): 559-66.

Blaha, P. Bigenzahn, S., et al. (2003). "The influence of immunosuppressive drugs on tolerance induction through bone marrow transplantation with costimulation blockade." Blood 101: 2886-2893.

Blazar, B. R., P. A. Taylor, et al. (1998). "Interleukin-10 dose-dependent regulation of CD4+ and CD8+ T cell-mediated graft-versus-host disease." Transplantation 66(9): 1220-9.

Davalli, A. M., L. Scaglia, et al. (1996). "Vulnerability of islets in the immediate posttransplantation period. Dynamic changes in structure and function." Diabetes 45(9): 1161-7.

Delovitch, T. L., B. Singh. (1997) "The nonobese diabetic mouse as a model of autoimmune diabetes: immune dysregulation gets the NOD" Immunity 6 (7): 727-738.

Gregori S., Giarratana N., et al. (2003) "Dynamics of pathogenic and suppressor T cells in development of autoimmune diabetes" J. Immunol 171: 4040-4047.

Groux, H., A. O'Garra, et al. (1997). "A CD4+ T-cell subset inhibits antigen-specific T-cell responses and prevents colitis." Nature 389(6652): 737-42.

Hackstein, H., T. Taner, et al. (2002). "Rapamycin inhibits macropinocytosis and mannose receptor-mediated endocytosis by bone marrow-derived dendritic cells." Blood 100(3): 1084-7.

Hempel, L., D. Korholz, et al. (1997). "High interleukin-10 serum levels are associated with fatal outcome in patients after bone marrow transplantation." Bone Marrow Transplant 20(5): 365-8.

Hojo, M., T. Morimoto, et al. (1999). "Cyclosporine induces cancer progression by a cell-autonomous mechanism." Nature 397(6719): 530-4.

Li, W., F. Fu, et al. (1999). "Recipient pretreatment with mammalian IL-10 prolongs mouse cardiac allograft survival by inhibition of anti-donor T cell responses." Transplant Proc 31(1-2): 115.

Lyons, A. B. Parish, C. R. (1994) "Determination of lymphocyte division by flow cytometry" J Immunol Methods 171: 131-137.

Moore, K. W., R. de Waal Malefyt, et al. (2001). "Interleukin-10 and the interleukin-10 receptor." Annu Rev Immunol 19: 683-765.

Roncarolo M. G., Battaglia M., et al. (2003) "The role of interleukin 10 in the control of autoimmunity" J. Autoimm 4: 269-272

Sehgal, S. N. (1998). "Rapamune (RAPA, Rapamycin, sirolimus): mechanism of action immunosuppressive effect results from blockade of signal transduction and inhibition of cell cycle progression." Clin Biochem 31(5): 335-40.

Shapiro, A. M., J. R. Lakey, et al. (2000). "Islet transplantation in seven patients with type 1 diabetes mellitus using a glucocorticoid-free immunosuppressive regimen." N Engl J Med 343(4): 230-8.

Taylor, P. A., C. J. Lees, et al. (2002). "The infusion of ex vivo activated and expanded CD4(+)CD25(+) immune regulatory cells inhibits graft-versus-host disease lethality." Blood 99(10): 3493-9.

Tisch, R. and H. McDevitt (1996). "Insulin-dependent diabetes mellitus." Cell 85(3): 291-7.

Trembleau, S., G. Penna, et al. (2000). "Early Th1 response in unprimed nonobese diabetic mice to the tyrosine phosphatase-like insulinoma-associated protein 2, an autoantigen in type 1 diabetes." J Immunol 165(12): 6748-55.

Wells, A. D., X. C. Li, et al. (1999). "Requirement for T-cell apoptosis in the induction of peripheral transplantation tolerance." Nat Med 5(11): 1303-7.

Yu, X., P. Carpenter, et al. (2001). "Advances in transplantation tolerance." Lancet 357(9272): 1959-63.

The invention claimed is:

1. A method of treating a subject affected by an autoimmune disease, comprising administering to said subject an effective amount of a combined pharmaceutical preparation comprising rapamycin, and at least one of IL-10 and IL-10 conjugated to polyethyleneglycol (PEG), as the sole active ingredients, wherein the effective amount induces an antigen-specific immune tolerance in said subject.

2. The method according to claim 1, wherein said autoimmune disease is selected from the group consisting of type I diabetes, rheumatoid arthritis, multiple sclerosis, and systemic lupus erythematosus.

3. The method according to claim 1, wherein the IL-10 is of human or viral origin.

4. The method according to claim 1, wherein the combined pharmaceutical preparation comprises IL-10 conjugated to polyethyleneglycol (PEG).

5. The method according to claim 1, wherein the antigen-specific immune tolerance is mediated by at least one of Tr1 cells and $CD4^+CD25^+$ Tr cells.

6. The method according to claim 1, wherein said pharmaceutical preparation is suitable for oral, intravenous, parenteral or subcutaneous administration.

7. The method according to claim 6, wherein said pharmaceutical preparation is in the form of a solution, suspension, tablet or capsule.

8. The method according to claim 1, wherein the effective amount of IL-10 is from 0.001 µg/kg to 1000 µg/kg and the effective amount of rapamycin is from 0.001 mg/kg to 100 mg/kg.

9. A method of treating a subject affected by an autoimmune disease, comprising:
administering to the subject an effective amount of a pharmaceutical preparation comprising a combination of active ingredients capable of inducing an antigen-specific immune tolerance in the subject, the active ingredients consisting of rapamycin, and at least one of IL-10 and IL-10 conjugated to polyethyleneglycol (PEG); and
inducing an antigen-specific immune tolerance in the subject.

10. The method according to claim 9, wherein the antigen-specific immune tolerance is maintained in the subject for at least 210 days after the subject received a final administration of the pharmaceutical preparation.

11. The method according to claim 9, wherein the antigen-specific immune tolerance is induced in the absence of administering FK506 to the subject.

12. The method according to claim 9, wherein the antigen-specific immune tolerance is induced in the absence of administering anti-IL2R to the subject.

13. The method according to claim 9, wherein the effective amount of the pharmaceutical preparation stimulates the production of $CD4^+$ Tr1 cells and $CD4^+CD25^+$ T cells in the subject.

14. A method of stimulating the production of $CD4^+$ Tr1 cells and $CD4^+CD25^+$ T cells in a subject suffering from an autoimmune disease, comprising:
administering to the subject an effective amount of a pharmaceutical preparation comprising a combination of active ingredients,
wherein, the active ingredients consist of rapamycin and IL-10, and
the stimulated production of $CD4^+$ Tr1 cells and $CD4^+CD25^+$ T cells induces antigen-specific immune tolerance in the subject.

\* \* \* \* \*